United States Patent [19]

Adelman et al.

[11] 4,352,940
[45] Oct. 5, 1982

[54] HYDROLYSIS OF METHYL ACETATE

[75] Inventors: Robert L. Adelman, Wilmington, Del.; Roy Segars, Jr., Seabrook, Tex.

[73] Assignee: E. I. Du Pont de Nemours and Company, Wilmington, Del.

[21] Appl. No.: 144,534

[22] Filed: Apr. 28, 1980

[51] Int. Cl.$^3$ ............... C07C 53/08; C07C 27/28; B01D 3/06
[52] U.S. Cl. .................... 562/607; 562/608; 203/88; 203/DIG. 6; 203/DIG. 23; 525/62; 568/877; 568/913
[58] Field of Search ............... 562/607, 608; 568/877, 568/913; 203/88, 16, 18, 80, 78, 71, 84, DIG. 23, DIG. 6; 525/62

[56] References Cited

U.S. PATENT DOCUMENTS

| | | | |
|---|---|---|---|
| 2,636,050 | 4/1953 | Hoaglin et al. | 568/913 |
| 2,650,249 | 8/1953 | Mention et al. | 562/607 |
| 2,936,321 | 5/1960 | Mercier | 562/607 |
| 3,052,610 | 9/1962 | Akaboshi et al. | 525/62 |
| 3,239,572 | 3/1966 | Zinsstag | 568/918 |
| 3,268,572 | 8/1966 | Knorr et al. | 568/913 |
| 3,317,593 | 5/1967 | Enk et al. | 562/606 |
| 3,350,445 | 10/1967 | Binning et al. | 203/69 |
| 3,438,870 | 4/1969 | Roscher et al. | 203/71 |

Primary Examiner—Wilbur L. Bascomb, Jr.

[57] ABSTRACT

In the hydrolysis of methyl acetate to acetic acid, the improvement comprising a flasher or stripper to separate methyl acetate and water from the hydrolyzer product stream and the recycle of these directly to the hydrolyzer.

2 Claims, 1 Drawing Figure

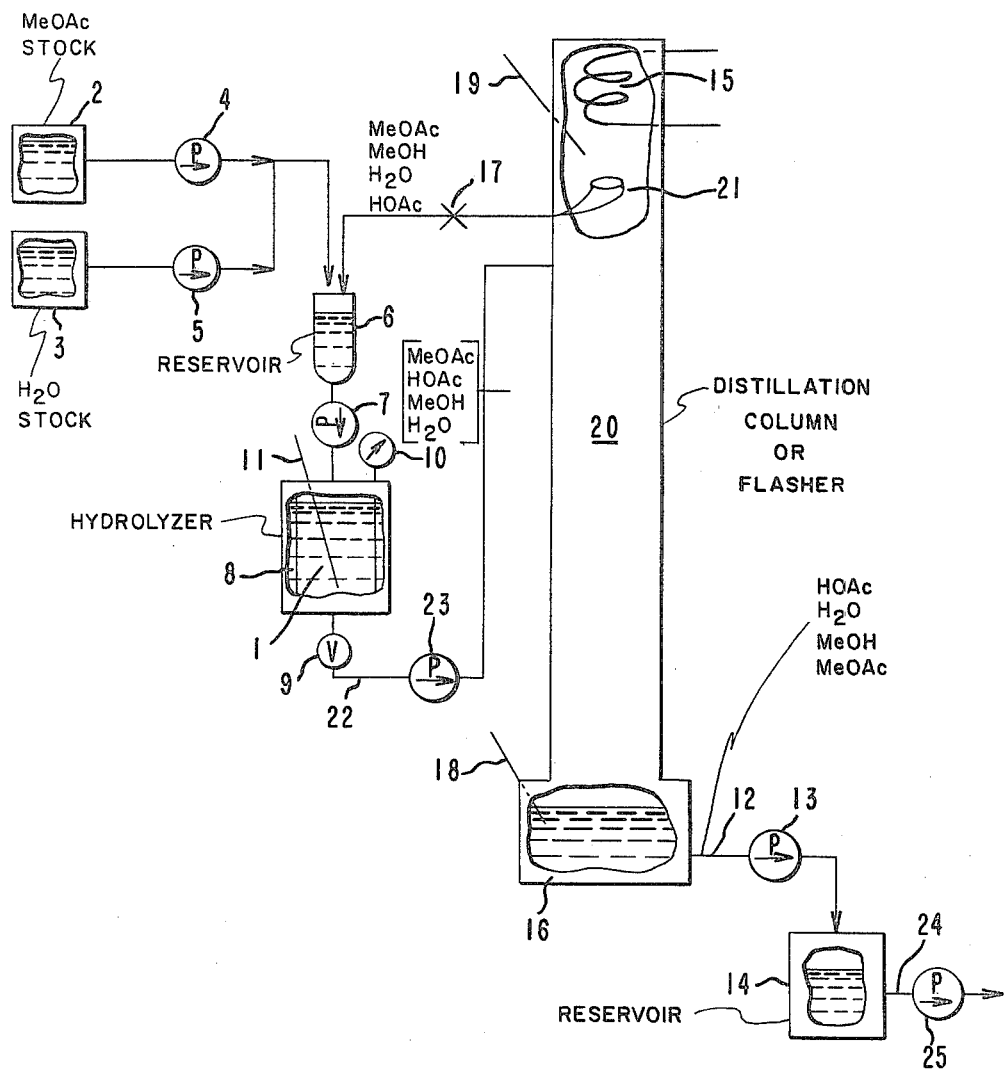

HYDROLYSIS OF METHYL ACETATE

BACKGROUND OF THE INVENTION

In the production of polyvinyl alcohol, methyl acetate is typically produced as a by-product. In order to produce polyvinyl alcohol at a reasonable cost, it is necessary to recover acetic acid and methanol from the methyl acetate so produced. This is typically done by the hydrolysis of methyl acetate with water to produce a mixture of methyl acetate, methanol, acetic acid and water, which mixture is subsequently separated to isolate the acetic acid and methanol. Effort has long been directed toward the improvement of the efficiency of this reaction and the subsequent separation. Since the hydrolysis process is an equilibrium reaction, it can be driven to greater acetic acid production by the addition of water. However, it is also desirable to keep the concentration of water to a minimum, since any water added to the system must later be removed from the reaction products. This removal is generally carried out by a distillation process in which any added volume increases the energy consumption.

SUMMARY OF THE INVENTION

The instant invention provides an improved process and apparatus for the hydrolysis of methyl acetate to produce acetic acid which gives increased conversion of methyl acetate with no additional water added to the reaction.

Specifically, the instant invention provides, in a process for the recovery of methanol and acetic acid from the methyl acetate by-product produced in the manufacture of polyvinyl alcohol by the hydrolysis of polyvinyl acetate in which methyl acetate is continuously hydrolyzed and the unreacted methyl acetate separated overhead by fractionation from methanol, acetic acid and water, and the methyl acetate recycled to the hydrolyzer, and methanol and acetic acid then separated by fractionation, the improvement which comprises feeding methyl acetate, water and optionally minor proportions of methanol and acetic acid to a liquid-filled hydrolyzer containing a cation exchange resin in the acid form and maintained at a temperature of about from 50° to 90° C., inclusive at a gauge pressure of about from 0 to 240 kPa, passing the effluent from the hydrolyzer to a separator or flasher, separating at least part of the unreacted methyl acetate and water overhead, optionally together with minor proportions of methanol and acetic acid, and directly recycling the recovered unreacted methyl acetate and water, optionally together with minor proportions of methanol and acetic acid, to the hydrolyzer while drawing off from the boiler of the separator or flasher a mixture of acetic acid, methanol, water and optionally methyl acetate and passing this to a fractionation column for the separation of methanol and optionally methyl acetate overhead from acetic acid and water in the boiler.

BRIEF DESCRIPTION OF THE DRAWING

The FIGURE is a schematic illustration of an apparatus which can be used in the present invention.

DETAILED DESCRIPTION OF THE INVENTION

The present invention is applicable to the conventional hydrolysis of methyl acetate. In accordance with this process, water is first added to the methyl acetate. The water serves two functions, first to aid in the separation of the methyl acetate from the methanol usually accompanying the methyl acetate and, secondly, to provide a reactant for the hydrolysis reaction. Hydrolysis results in a mixture containing unreacted methyl acetate, methanol, acetic acid and water. This mixture is then separated to isolate the acetic acid and methanol. The general hydrolysis process is discussed, for example, in C. A. Finch, "Polyvinyl Alcohol, Properties and Application", Wiley & Sons, New York (1971) pp. 129–135, hereby incorporated by reference.

The feedstream used in the instant process generally comprises about from 45 to 95% methyl acetate, and preferably about from 60 to 85%. The feestream also comprises water, generally in a concentration of about from 5 to 60%, and preferably about from 10 to 40%. The molar ratios of water to methyl acetate should be in the range of about from 0.5 to 10.0, and preferably about from 1.0 to 4.5. The feed mixture can also contain up to about 20 wt. % of methanol, 15 wt. % acetic acid, and 1–2 wt. % acetaldehyde.

The hydrolysis catalyst used in the instant invention can be selected from a wide variety of acid cation exchange resins which have been previously used for hydrolysis reactions of this type. Preferred resins include crosslinked styrene sulfonic acid gels, 4% and 8% crosslinked with divinyl benzene; sulfonated phenol-formaldehyde condensation products; and macroreticular resins such as highly crosslinked styrene sulfonic acid resins. In general, a catalyst size of from 10–125 mesh can be used. A particularly preferred catalyst is a gel-type crosslinked polystyrene sulfonic acid, 8% crosslinked, having a 20–50 mesh particle size and a salt exchange capacity of 5 millequivalents of acid per gram of dry resin.

The hydrolyzer in the instant invention is maintained at a temperature of about from 50° to 90° C. Temperatures below this range generally provide an unacceptably slow reaction rate while higher temperatures contribute to undesirable by-product formation and catalyst degradation. The pressure in the hydrolyzer is not critical to the present invention, and is generally maintained in a range from about atmospheric pressure to 689 kPa (100 psi).

In accordance with the present invention, the effluent from the hydrolyzer, generally a mixture of methyl acetate, methanol, acetic acid and water, is passed to a separator or flasher to separate at least part of the unreacted methyl acetate with water overhead, optionally together with minor proportions of methanol and acetic acid. This overhead fraction is directly recycled to the hydrolyzer. From the boiler of the separator or flasher a mixture of acetic acid, methanol, water and optionally methyl acetate is removed and passed to other separation apparatus for the isolation of acetic acid and methanol.

The particular configuration of the separator or flasher will vary with the size of the overall apparatus. The column can contain a packed bed, including, for example, Raschig rings, sieve plates, or screens. The size and packing of the column should be sufficient to provide an overhead vapor having a methyl acetate concentration of at least about 80%, and preferably about from 82 to 92% by weight.

The present invention will be further understood by reference to the FIGURE, which is a schematic drawing of the process and apparatus of the present invention.

In that FIGURE, reactor (1) is filled with cation exchange resin in acid form as catalyst for the hydrolysis of methyl acetate (MeOAc). The reactor is fed with reactants from reservoir (6) by pump (7). The reactants are the MeOAc stock feed from container (2) pumped to reservoir (6) by pump (4), water from container (3) pumped to reservoir (6) by pump (5) and recycled MeOAc from reflux collector (21) below reflux condenser (15) at top of distillation column (20) fed through variable takeoff (17) to reservoir (6). When operating above atmospheric pressure, the reactants are pumped by pump (7) at a rate which maintains the level of reactants in reservoir (6) constant. The reactor (1) is maintained liquid full and is heated externally by jacket (8), which can be a heated oil or water jacket or an electrical tape, to the desired temperature measured by thermocouple (11). The desired pressure is determined by the pressure inside reactor (1) which is controlled by the in-line pressure valve (9) and observed on pressure gauge (10). For the hydrolysis of MeOAc, the reaction temperature in reactor (1), is maintained between 50° and 90° C., inclusive and the gauge pressure is 0-241 kPa (0-35 psi). The hydrolysate flows from reactor (1) through line (22) to column (20) at a point below collector (21); the column is fitted with boiler (16), reflux condenser (15), collector (21), with variable takeoff (17). The walls of the column and the boiler are externally heated sufficiently to produce a reflux of unreacted MeOAc to collector (21) and a mixture of acetic acid (HOAc), methanol (MeOH), water (H$_2$O) and optionally MeOAc as hydrolysate product in boiler (16). This hydrolysate product is pumped from boiler (16) by pump (13) through line (12) to product reservoir (14) at a rate which maintains the liquid level in boiler (16) constant. The temperature of the boiler is measured by thermocouple (18) and in the head of the column by thermocouple (19). The column is operated at substantially atmospheric pressure at the head. The hydrolysate product comprising HOAc, MeOH, H$_2$O and optionally MeOAc is pumped from product reservoir (14) through line (24) by pump (25) to a standard fractionation column in which MeOH and optionally MeOAc and H$_2$O is recovered overhead. Alternatively MeOH alone is recovered overhead, and the HOAc-H$_2$O in the boiler can be separated by conventional procedures.

When operating reactor (1) at atmospheric pressure, pump (7) and pressure relief valve (9) are eliminated but a pump (23) is placed in line (22) after the reactor and adjusted to keep the liquid level in reservoir (6) constant.

In either mode of operation, the reactor is filled with the liquid phase and the hydrolysis is carried out entirely in the liquid phase. The process can be operated to convert 100% of the MeOAc from stock to MeOH and HOAc. If the process is run at less than 100% conversion of MeOAc, the product stream from the head of the MeOH fractionation column after reservoir (14) can be pumped to an extraction still, operated according to known art, to separate MeOAc from MeOH and the recovered MeOAc also pumped to reservoir (6).

The present invention provides a high conversion of methyl acetate and water to acetic acid and methanol combined with high throughput rates and productivity. In addition, a relatively low ratio of water to methyl acetate can be used in the feed, thus reducing the energy requirements of the entire system.

The present invention is further illustrated by the following specific examples, in which parts and percentages are by weight unless otherwise indicated.

EXAMPLE 1

An apparatus substantially as shown in the FIGURE was operated at atmospheric pressure to hydrolyze methyl acetate. The hydrolyzer was a water-jacketed reactor, 10 cm high and 8 cm in diameter, filled with 426 g of styrene sulfonic acid gel-type resin, 8% crosslinked with divinyl benzene. The catalyst was 20–50 mesh, and had a moisture content of 52% and a salt exchange capacity of 5.0 meq/g dry resin. The hydrolyzer was operated at an internal temperature of 53° C. The separator was a cylinder 74 cm high and 5.7 cm in diameter, filled with ¼" glass Raschig rings, and wrapped with flexible heating tape. The bottom of the column was heated with a heating mantle to maintain the internal liquid at 82° C. A feed was added made up of 96.5% methyl acetate, 1.2% methanol, and 2.3% acetic acid, added at a rate of 2.8 cc per minute. This was combined with water added at a rate of 2 cc per minute. This provided a water/methyl acetate mole ratio of 3.3 and an overall feed composition added to the hydrolyzer of 54.4/43.7/0.7/1.3 methyl acetate/water/methanol/acetic acid.

The reflux ratio was about 2/1. The recycle rate back to the hydrolyzer from the top of the condenser was 21.2 g/min, with a composition of 83.0/3.5/13.5 MeOAc/H$_2$O/MeOH by wt. The ratio of MeOAc in recycle to MeOAc in the feed was therefore 7:1. Analysis of the final effluent from the unit was 4.3/31.5/22.2/42.0 by wt MeOAc/H$_2$O/MeOH/HOAc. The analysis was carried out by wet analysis for the HOAc, mass law calculation for the other components, and confirmed by gas chromatography for all components. The process gave a MeOAc conversion of 92%, a productivity of 7.8 g HOAc/g damp resin-day, and a throughput rate of 15.5 g total feed/g damp resin-day.

EXAMPLE 2

The procedure of Example 1 was repeated, except that a mole ratio of water to methyl acetate in the feed of about 4:1 was used. 96–100% conversions of methyl acetate were obtained.

EXAMPLE A

The general procedure of Example 1 was repeated, except that the apparatus used did not contain the separator (20). At equivalent throughput rates and temperature, a methyl acetate conversion of 47% was obtained.

EXAMPLE 3

The general procedure of Example 1 was repeated, except that the water to methyl acetate ratio in the feed was about 4.1 to 1, using a water feed of 2.5 cc/min. The separator liquid temperature was 87° C. and the reflux temperature 63° C. The percent HOAc in the effluent from the entire unit was 42%, corresponding to a 100% conversion of the MEOAc. The productivity was 8.7 g HOAc/g damp resin-day, at a throughput rate of 17.2 g total feed/g damp resin-day.

EXAMPLE 4

The general procedure of Example 1 was repeated, except that the temperature in the resin bed was 79° C., and the temperature in the column pot was 67° C. The pressure in the reactor section was held at 261.8 kPa (38 psig) by the in-line release valve. The overall feed composition (by wt) was 71.4/25.9/0.9/1.8 MeOAc/$H_2O$/MeOH/HOAc, obtained by a stock feed composition of 96.5/1.2/2.3 MeOAc/MeOH/HOAc at 12.6 cc/min, combined with a $H_2O$ feed of 4.1 cc/min. The $H_2O$/MeOAc mole ratio in the feed was 1.51. The recycle rate into the hydrolyzer was 24 g/min, and the composition of this recycle stream was 87.2/2.7/10.1 MeOAc/$H_2O$/MeOH. The ratio of MeOAc recycle back to the hydrolyzer/fresh MeAc in the feed was 1.9.

The composition of the liquid leaving the entire unit was (by wt) 37.8/18.0/15.2/29.0 MeOAc/$H_2O$/MeOH/HOAc. Thus the MeAc conversion was 46.9%. Productivity was 53 g HAc formed/g damp resin-day, and throughput rate was 159.3 g total fresh feed/g damp resin-day.

We claim:

1. In a process for the recovery of methanol and acetic acid from methyl acetate in which methyl acetate is continually hydrolyzed and methanol and acetic acid separated from the resulting mixture of methanol, acetic acid, water and unreacted methyl acetate, the improvement which comprises feeding methyl acetate, water and optionally minor proportions of methanol and acetic acid to a liquid-filled hydrolyzer containing a cation exchange resin in the acid form and maintained at a temperature of about from 50°–90° C., inclusive at a gauge pressure of about from 0 to 240 kPa to produce a mixture of methanol, acetic acid, water, and unreacted methyl acetate, continuously distilling the mixture in a distillation column or flasher, continuously removing an overhead mixture of methyl acetate, water, methanol and, optionally, minor amounts of acetic acid from the top of the distillation column or flasher and returning the overhead mixture directly to the hydrolyzer, and withdrawing from the bottom of the distillation column or flasher a bottom mixture of acetic acid, water, methanol and optionally methyl acetate.

2. A process of claim 1 wherein the bottom mixture is substantially free of methyl acetate.

* * * * *